United States Patent [19]

Grosse

[11] 4,371,509

[45] Feb. 1, 1983

[54] OXIDIZING PHOSPHORUS COMPOUNDS WITH CHLOROSULFONIC ACID

[75] Inventor: Jürgen Grosse, Hürth, Fed. Rep. of Germany

[73] Assignee: Hoechst Aktiengesellschaft, Fed. Rep. of Germany

[21] Appl. No.: 299,678

[22] Filed: Sep. 8, 1981

[30] Foreign Application Priority Data

Sep. 10, 1980 [DE] Fed. Rep. of Germany ....... 3033957

[51] Int. Cl.$^3$ .......................... C07F 9/09; C07F 9/42; C07F 9/28; C01B 25/10
[52] U.S. Cl. ................................ 423/300; 260/543 P; 260/985; 568/14
[58] Field of Search .................... 260/985, 543 P, 947; 423/300; 568/14

[56] References Cited

U.S. PATENT DOCUMENTS

| | | | |
|---|---|---|---|
| 2,694,084 | 11/1954 | Brugmann | 260/985 |
| 2,844,617 | 7/1958 | Jonas et al. | 260/985 |
| 2,909,555 | 10/1959 | Scott | 260/985 |
| 2,952,699 | 9/1960 | Norman | 260/985 |
| 3,423,485 | 1/1969 | Herweh et al. | 260/947 |
| 3,658,951 | 4/1972 | Herweh | 260/947 |

FOREIGN PATENT DOCUMENTS 979249 1/1965 United Kingdom ............... 423/300

OTHER PUBLICATIONS

Herweh, "J. Org. Chem.", vol. 31 (1966), pp. 2422-2424.

*Primary Examiner*—Joseph E. Evans
*Attorney, Agent, or Firm*—Connolly and Hutz

[57] ABSTRACT

The invention relates to a process for oxidizing organic phosphorus compounds of the general formula (I)

$$R_{3-n}PX_n \quad (I)$$

in which R stands for an organic radical, X stands for halogen and n stands for 0, 1, 2 or 3, to obtain compounds of the general formula (II)

$$R_{3-n}P(O)X_n \quad (II)$$

in which R, X and n have the meanings given above. To this end, chlorosulfonic acid is used as oxidant and the oxidation is effected in homogeneous liquid phase.

3 Claims, No Drawings

OXIDIZING PHOSPHORUS COMPOUNDS WITH CHLOROSULFONIC ACID

The present invention relates to a process for oxidizing phosphorus compounds of the general formula (I)

$$R_{3-n}PX_n \quad (I)$$

in which R stands either for rectilinear and/or branched alkyl-, cycloalkyl-, aryl-, alkylaryl- as well as aralkyl groups having from 1 to 18 carbon atoms, preferably from 1 to 8 carbon atoms, or for a group —OR' or —SR', in which R' stands for an aryl radical or alkyl radical having from 1 to 8 carbon atoms, or in which R stands for a group

in which R" stands for an alkyl radical having from 2 to 8 carbon atoms, X stands for halogen, especially for chlorine, bromine or iodine, and n stands for 0, 1, 2 or 3, so as to obtain compounds of the following general formula (II)

$$R_{3-n}P(O)X_n$$

in which R, X and n have the meanings given above.

It has already been described that compounds of the general formula (I) can be oxidized with the use of oxidants, such e.g. as $O_2$, $NO$, $NO_2$, $SO_2$, $SO_2Cl_2$, $SO_3$ (cf. e.g. Houben-Weyl, Methoden der organischen Chemie, volumes 12/1 and 12/2, and Kosolapoff/Maier, Organic Phosphorus Compounds, Wiley-Interscience, 1972).

These known processes are beset with a series of disadvantages. The oxidants most commonly used therein are gases so that it is necessary for the oxidations to be effected as gas/liquid-reactions. In order to achieve high reaction velocities, it is invariably necessary for large gas volumes to be put through within short periods of time, or for the reaction to be effected under increased pressure, naturally with the use of technically expensive apparatuses. Especially in the event of a relatively volatile compound of formula (I) being used, the reaction is liable inter al alia to entail explosive outbreaks in the gas chamber whenever unduly large proportions of the compound of formula (I) become introduced thereinto. In order to avoid heavy loss of desirable product, it is additionally necessary in these prior processes to use efficient off-gas coolers which permit the carrying along of volatile compounds either of formula (I) or (II) to be inhibited.

In addition to this, the oxidants specified above are often not generally useful for the oxidation of compounds of formula (I); indeed they sometimes just permit oxidizing individual representatives of these compounds.

EP-A 0 010 368, for example, describes a process for oxidizing phenyldichlorophosphane at atmospheric pressure with oxygen so as to obtain phenyl phosphoric acid dichloride in accordance with the following equation:

$$2\ C_6H_5PCl_2 + O_2 \xrightarrow{\text{about 30-60}^\circ\text{ C.}} 2\ C_6H_5P(O)Cl_2$$

In the event of the reaction being effected with $CH_3PCl_2$, the yield of desirable product is seriously impaired by $CH_3PCl_2$ which is expelled. In addition to this, long reaction periods are necessary until the reaction is complete (cf. Houben-Weyl, volume 12/1, page 398: 86% yield after reaction for 24 hours). Tests made on this reaction have additionally shown it often to give rise to explosive outbreaks.

The oxidation of $CH_3PBr_2$ by means of $NO_2$ (L. Maier, Helv. Chem. Acta 46, page 2667 (1963)) entails considerable loss of desirable final product due to P-C-cleavage (yield 70% of theoretical).

The oxidation by means of $SO_2Cl_2$ in accordance with the following equation:

$$C_6H_5PCl_2 + SO_2Cl_2 \rightarrow C_6H_5P(O)Cl_2 + SOCl_2$$

involves formation of thionyl chloride which has to be separated distillatively from the desired final product (V.A. Petrov et al. Chem Abs., page 5883 h (1962).

$SO_3$ is difficult to handle technically and expensive.

Another known process for oxidizing compounds of type I comprises subjecting the compounds first to chlorination and then to hydrolysis (cf. Houben Weyl, Methoden der organischen Chemie, volume 12/1, page 390) in accordance with the following equations:

(a) $RPCl_2 \xrightarrow{\text{chlorination}} RPCl_4$ (b) $RPCl_4 \xrightarrow[SO_2]{H_2O} RPOCl_2 + 2\ HCl$ or $\longrightarrow RPOCl_2 + SOCl_2.$ This is a complicated procedure which is required to be carried out in at least two stages.

The oxidation with $SO_2$ results in product mixtures (E. Fluck, H. Binder, Angew. Chemie, 77, page 381 (1965) in accordance with the following equation:

$$3C_6H_5PCl_2 + SO_2 \rightarrow 2C_6H_5P(O)Cl_2 + C_6H_5P(S)Cl_2$$

and needs extremely long reaction periods (42 days).

In addition to this, it is known that $PCl_3$ can be oxidized with oxygen in the presence of hydrocarbons (Houben Weyl, vol. 12/1, page 399) in accordance with the following equation:

$$R-H + 2PCl_3 + O_2 \rightarrow RP(O)Cl_2 + POCl_3 + HCl.$$

This is a process wherein the yield is as low as 18 to 45% of the theoretical.

It is therefore an object of the present invention to provide a process which avoids the adverse effects described hereinabove.

This object can unexpectedly be achieved in very simple manner by the use of chlorosulfonic acid as an oxidant and by effecting the reaction, optionally in the presence of a solvent, in homogeneous liquid phase.

It is preferable for the reaction to be effected at temperature of between $-30^\circ$ and $150^\circ$ C., and for the reaction components comprising chlorosulfonic acid and organic phosphorus compound of the above formula (I) to be used in a molar ratio of 1:1 to 1:1.1. The products of general formula (II) obtained by the present process are interesting intermediates for making plant protective agents, flameproofing agents or plastics additives.

The substances of formula (I) used as starting material are known compounds which can be made by generally accepted methods of organophosphorus chemistry.

The process of the present invention compares favorably with the prior art methods in respect of the following points:

The reactions always occur in a homogeneous liquid phase, at high speed. The reaction products which are commonly obtained in quantitative yield are very pure so that it is often unnecessary for them be be subjected to purifying treatment, such as distillation. In many cases, it is sufficient for the reaction products to be subjected to short stripping under vacuum so as to obtain very pure final material with an unexpectedly low residual sulfur content therein.

The invention provides for the compounds of formula (I) which are to undergo oxidation to be admixed with metered proportions of chlorosulfonic acid, or inversely for the chlorosulfonic acid to be admixed with metered proportions of the formula (I) compounds. Sometimes, it may be advantageous to meter the two reactants jointly into the reactor which may have final product placed therein.

Once the necessary temperature has been reached, the reaction is initiated at once; it takes an exothermal course with continuous evolution of gas, desirable product of formula (II) remaining behind.

In the event of the compounds of formula (I) being volatile, it may prove advantageous to meter the chlorosulfonic acid oxidant into the gas outlet so as to minimize the loss of desirable final product which is liable to be carried along by low-boiling starting material. Under circumstances, it is good practice for a scrubbing column to be disposed in the gas outlet. In this way, it is possible for reactive contact to be produced therein between the oxidant and co-expelled component (I) material and for the latter to be washed out from the off-gas containing HCl and $SO_2$. The reaction can incidentally be effected in the absence of any solvent or in the presence of an inert solvent.

The following Examples illustrate the invention:

EXAMPLE 1

331 g (2.83 mols) methyldichlorophosphane and 327 g (2.82 mols) chlorosulfonic acid were jointly introduced dropwise with agitation into a 1 liter multinecked flask provided with an agitator, internal thermometer, reflux condenser and 2 dropping funnels, and reacted therein. The chlorosulfonic acid was more particularly admitted via the reflux condenser through which off-gas escaped. The reaction temperature was maintained at about 25° to 30° C. by cooling. After dropwise addition over 1 hour, the whole was stirred for a further 1 hour at room temperature. Next, the crude product was stripped at 32° C. under a pressure of 0.5 millibar.

371 g (99% of the theoretical) methanephosphonic acid dichloride of 99.4% (determined by gas chromatography) was obtained. The product was allowed to stand overnight and found to crystallize (melting point: 32° C.). It contained 0.4% residual sulfur.

EXAMPLE 2

58.25 g (0.5 mol) chlorosulfonic acid was placed in a 1 liter multinecked flask provided with an internal thermometer, dropping funnel, stirrer and reflux condenser. Next, 58.5 g (0.5 mol) methyldichlorophosphane was added dropwise while cooling with water at a temperature inside the flask of 20° C. and with agitation. Following this, a further 699 g (6 mols) chlorosulfonic acid was added which was admixed dropwise within 4 hours with 702 g (6 mols) methyldichlorophosphane, as described above. After a reaction period of 1 hour, the product was stripped at 32° C. under a pressure of up to 130 millibars.

820 g (95% of the theoretical) methane phosphonic acid dichloride of 99.1% (determined by gas chromatography) was obtained. The product was allowed to stand overnight and found to crystallize (melting point: 30° C.).

EXAMPLE 3

1228 g (10.5 mols) methyldichlorophosphane and 1165 g (10.0 mols) chlorosulfonic acid were jointly introduced dropwise into a 2 liter multinecked flask provided with a stirrer, internal thermometer, dropping funnel, and a 15 cm Raschig column provided with an intense cooler and dropping funnel mounted thereon, and cooling bath. The chlorosulfonic acid was admitted via the reflux cooler and the 15 cm Raschig column. The temperature in the flask was maintained at less than 30° C. by cooling. The introduction period was 3 hours. After a post reaction time of 1 hour at 35° C. under a pressure of 130 millibars, the whole was stripped for 30 minutes 1324 g (99.6% of the theoretical) methanephosphonic acid dichloride of 99.4% (determined by gas chromatography) which gradually crystallized was obtained (melting point: 31° C.). The product contained less than 0.03% residual sulfur.

EXAMPLE 4

49.5 g (0.42 mol) chlorosulfonic acid and 100 ml dichloromethane were placed in a 250 ml multinecked flask provided with a stirrer, internal thermometer, reflux concenser and dropping funnel and admixed dropwise within 30 minutes with 41 g (0.42 mol) dimethylchlorophosphane. The reaction temperature was maintained at 15° to 20° C. by cooling. Next, the whole was after-stirred for 2 hours at room temperature. The solvent was removed at 80° C. under a pressure of 130 millibars. 45 g (95% of the theoretical) dimethylphosphinic acid chloride of 97.8% (determined by gas chromatography) was obtained.

EXAMPLE 5

46.4 g (0.4 mol) chlorosulfonic acid was placed in an apparatus as described in Example 4 and reacted therein with 54 g (0.41 mol) ethyldichlorophosphane at 20°–30° C. The introduction period was 80 minutes. After a post reaction time of 30 minutes, the whole was stripped at 30° C. under a pressure of 130 millibars. 57 g (97% of the theoretical) ethanephosphonic acid dichloride was obtained. $^{21}$P-NMR-spectroscopy indicated that the product was free from impurities.

EXAMPLE 6

35.8 g (0.2 mol) phenyldichlorophosphane was placed in an apparatus as described in Example 4 and reacted therein while cooling with 23.4 g (0.2 mol)

chlorosulfonic acid at 25°-30° C. The introduction period was 30 minutes. After a post reaction time of 1 hour, the whole was stripped at 35° C. under a pressure of 33 millibars. 39 g (0.2 mol) phenylphosphonic acid dichloride of 98.2% (determined by gas chromatography was obtained.

EXAMPLE 7

116.5 g (1 mol) chlorosulfonic acid was placed in an apparatus as described in Example 4 and preheated to 50° C. Next, 137.5 g phosphorus trichloride was added dropwise within 1.5 hours, the reaction temperature being maintained at about 30° C. by cooling after the reaction had been initiated at about 50° C. Next, the whole was refluxed and distilled for 30 minutes up to a head temperature of 74° C. 130 g crude phosphorus oxide chloride of 85% (determined by gas chromatography) was obtained.

EXAMPLE 8

0.2 mol phosphorus tribromide was placed in an apparatus as described in Example 4 and reacted therein with 0.2 mol chlorosulfonic acid at 45°-47° C. After an introduction period of 30 minutes and a post-reaction time of 30 minutes, the product commenced crystallizing at about 35° C. It was stripped at 35° C. up to a pressure of 30 millibar. 50 g crude phosphorus oxide bromide (melting point: 48° C.) was obtained. $^{31}$P-NMR spectroscopy indicated that the product contained 73% P in the form of $P(O)Br_3$.

EXAMPLE 9

80 g (0.45 mol) S-propylthiophosphorous acid ester dichloride was placed in an apparatus as described in Example 4 and reacted therein while cooling with 52.6 g (0.45 mol) chlorosulfonic acid at 18°-20° C. The introduction period was 30 minutes. After a post reaction time of 30 minutes, the whole was stripped at 30° C. under a pressure of up to 100 millibar. 86 g crude product was obtained. $^{31}$P-NMR-spectroscopy indicated that it contained 73% P in the form of S-propylthiophosphoric acid ester dichloride.

EXAMPLE 10

23.3 g (0.2 mol) chlorosulfonic acid was placed in an apparatus as described in Example 4 and admixed dropwise within 1 hour with 62 g (0.2 mol) triphenyl phosphite while cooling. After a reaction period of about 20 minutes, the reaction mixture became viscous so that it was necessary for it to be admixed with 20 ml dichloromethane as a solvent. The reaction temperature was maintained at 25°-30° C. After a post reaction period of 1 hours, the whole was stripped at 35° C. under a pressure of up to 100 millibars. 70 g crude product was obtained.

$31^P$-NMR-spectroscopy indicated that it contained 65% P in the form of triphenyl phosphate.

EXAMPLE 11

116.5 g (1 mol) chlorosulfonic acid was placed in an apparatus as described in Example 4 and reacted therein within 60 minutes with 208 g (1 mol) tributylphosphane at 18°-20° C. while cooling with ice. Towards the end of the reaction when cooling was stopped, the reaction temperature rose to 34° C. The whole was stripped at 70° C. under a pressure of 0.5 millibar. This was accompanied by a violent exothermal reaction. The temperature rose up to 140° C. The material was stripped once again at 80° C. under a pressure of 1 millibar. 263 g tributylphosphane oxide was obtained in the form of a HCl-adduct (determined by elementary analysis and $31^P$-NMR-spectroscopy). 90% P was in the form of a tributylphosphane oxide HCl-adduct.

EXAMPLE 12

23.3 g (0.2 mol) chlorosulfonic acid in 40 ml dichloromethane was placed in the standard apparatus (Example 4) and admixed dropwise within 45 minutes with 72 g (0.2 mol) tri-n-octylphosphane while stirring. The temperature was maintained at less than 30° C. by gentle cooling. After a post reaction period of 1 hour, the whole was stripped at 95° C. under a pressure of 1.3 millibar. 77 g crude product was obtained. $31^P$-NMR-spectroscopy indicated that it contained 91% P in the form of a tri-n-octylphosphane oxide HCl-adduct.

EXAMPLE 13

0.75 mol chlorosulfonic acid was placed in the standard apparatus (Example 4) and admixed dropwise within 35 minutes with 0.75 mol 2-chloro-1,3,2-dioxaphospholane at 22°-28° C. while cooling. After a post reaction period of 45 minutes, the whole was stripped at 65° C. under a pressure of 30 millibars. 109 g slightly yellowish crude product was obtained. $31^P$-NMR-spectroscopy indicated that it contained 75% P in the form of 2-chloro-2-oxo-1,3,2-dioxaphospholane.

We claim:

1. A process for oxidizing phosphorus compounds of the general formula (I)

$$R_{3-n}PX_n \qquad (I)$$

in which R stands either for rectilinear and/or branched alkyl-, cycloalkyl-, aryl-, alkylaryl- as well as aralkyl groups having from 1 to 18 carbon atoms, or for a group —OR' or —SR', in which R' stands for an aryl radical or alkyl radical having from 1 to 8 carbon atoms, or two R groups together stands for a group

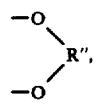

in which R" stands for an alkylene radical having from 2 to 8 carbon atoms, X stands for halogen, and n stands for 0, 1, 2 or 3, so as to obtain compounds of the following general formula (II)

$$R_{3-n}P(O)X_n \qquad (II)$$

in which R, X and n have the meanings given above, which comprises using chlorosulfonic acid as an oxidant and effecting the oxidation in homogeneous liquid phase.

2. The process as claimed in claim 1, wherein the oxidation is effected a temperatures within the range −30° and 150° C.

3. The process as claimed in claim 1, wherein the reactants comprised of chlorosulfonic acid and organic phosphorus compound of formula (I) are used in a molar ratio of 1:1 to 1:1.1.

* * * * *